Figure 3:
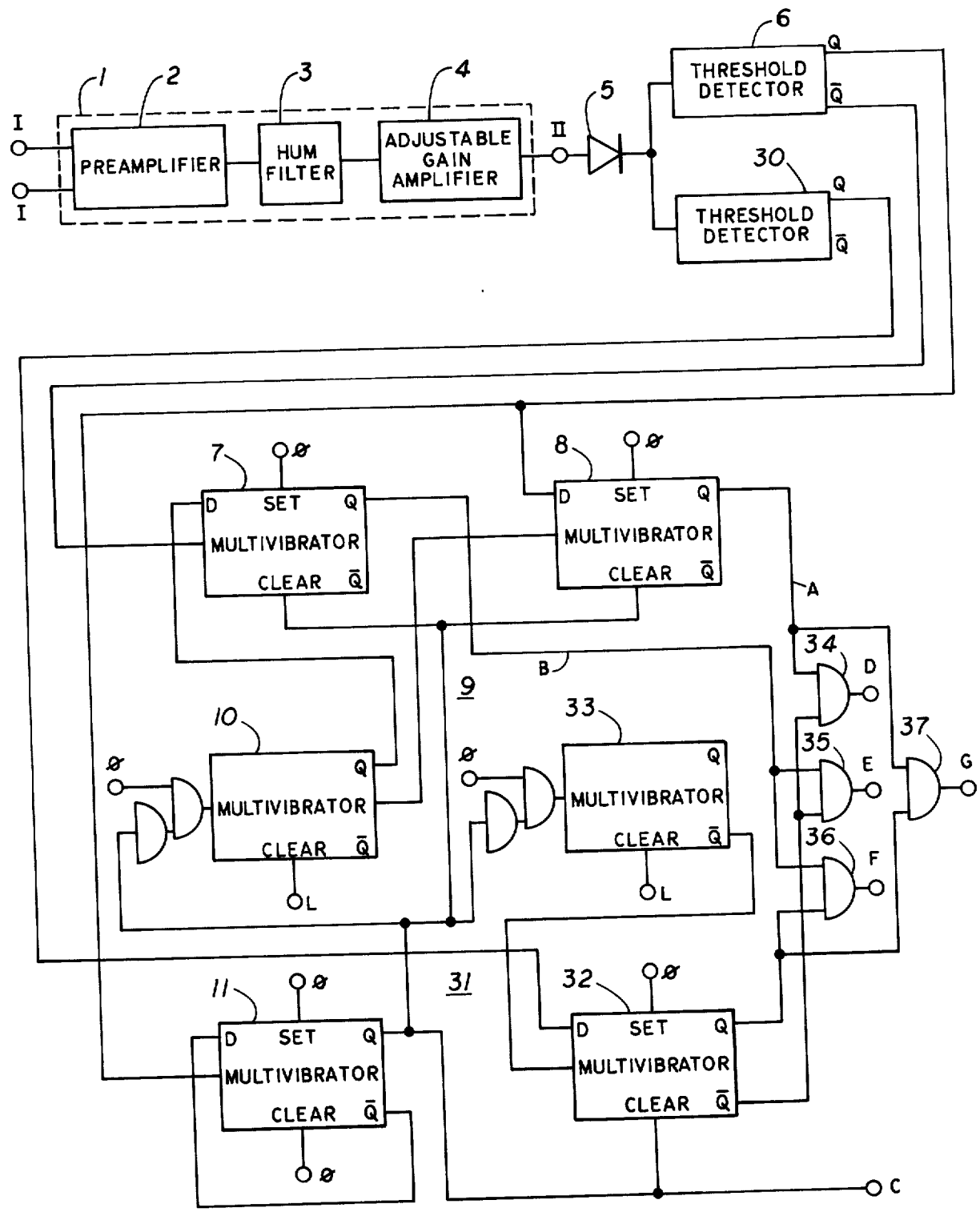

United States Patent [19]

Goles

[11] 4,087,730
[45] May 2, 1978

[54] ELECTRIC CONTROL CIRCUIT
[75] Inventor: Norbert Goles, Vienna, Austria
[73] Assignee: Viennatone Gesellschaft m.b.H., Vienna, Austria
[21] Appl. No.: 725,106
[22] Filed: Sep. 20, 1976
[30] Foreign Application Priority Data
Sep. 18, 1975 Austria .................... 7184/75
[51] Int. Cl.² .................... G05B 19/28; A61F 1/00
[52] U.S. Cl. .................... 318/603; 3/1.1
[58] Field of Search .................... 3/1.1; 318/600, 601, 318/603; 235/151.11 M
[56] References Cited
U.S. PATENT DOCUMENTS
3,820,168 6/1974 Horvath .................... 3/1.1

OTHER PUBLICATIONS

"The Use of Myselectric Currents", Battye, et al, Journal of Joint and Bone Surgery, vol. 37-B, No. 3, pp. 506-510, 1955.

"A Three-State Myo-Electric Control," Dorcas et al., Med. and biol. Engng., vol. 4, pp. 367-370, Jul. 1966.
"Electro-Control: an Eng—Controlled A/K Prosthesis," Horn, Med. and biol. Engng., vol. 10, pp. 61-77, 1972.

Primary Examiner—Robert K. Schaefer
Assistant Examiner—John J. Feldhaus
Attorney, Agent, or Firm—Kurt Kelman

[57] ABSTRACT

At least one comparator circuit and one timing circuit are provided so that the operation of a control element in response to the tensing of the muscles of a patient depends upon the time duration during which the patient tenses the muscle. Further timing and comparator circuits may be provided so that the rate at which the patient tenses the muscles can also influence the operation of the output control element. A reset circuit resets the timing and comparator circuits in response to alternate muscle tensings, allowing the patient free choice of any available operating condition independent of the previous operating condition.

10 Claims, 13 Drawing Figures

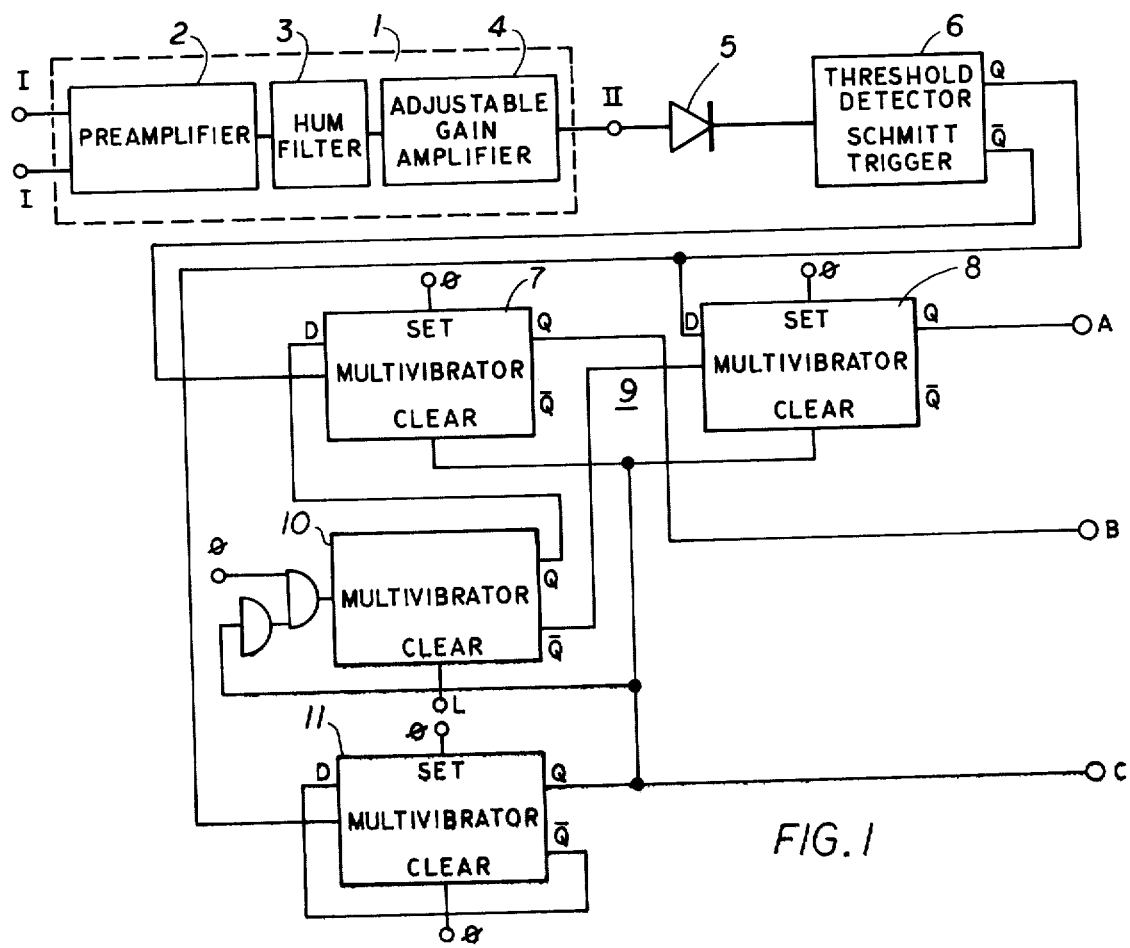
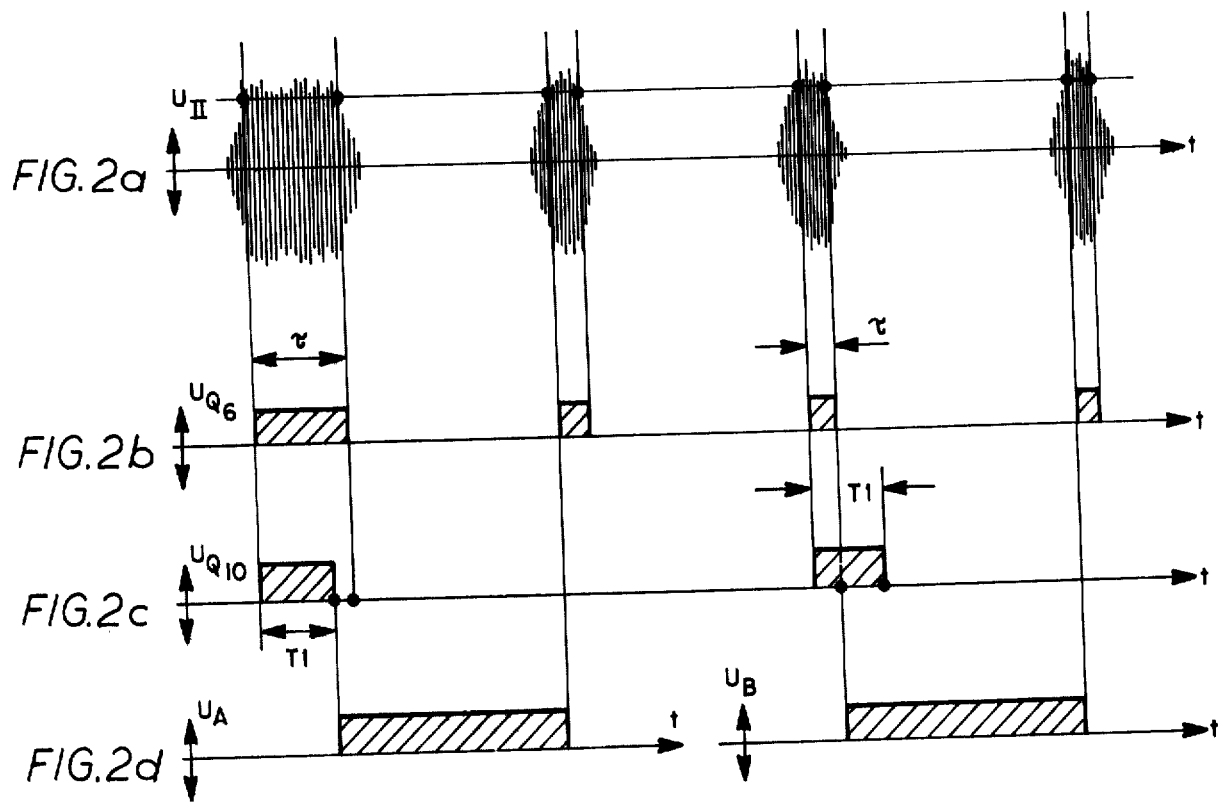

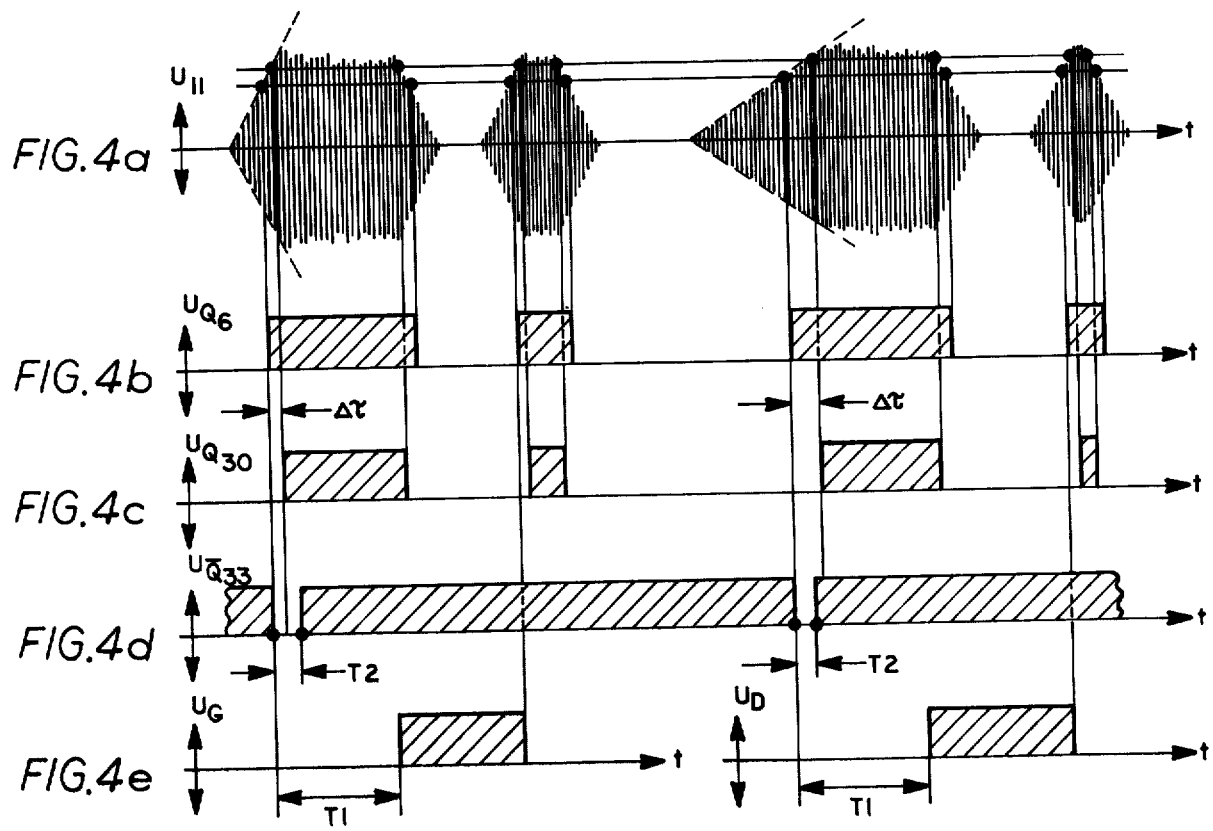
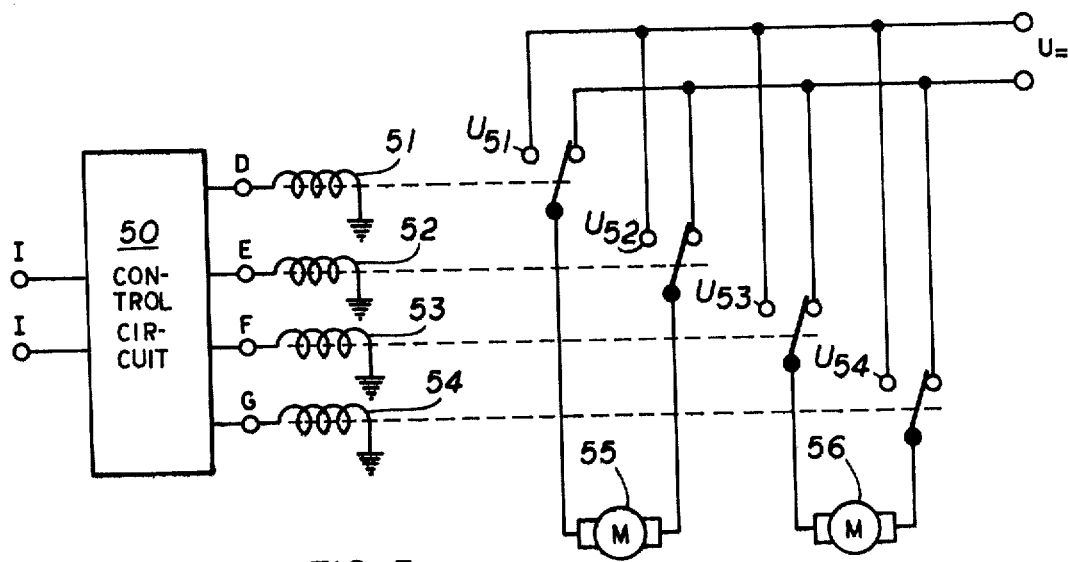
FIG. 5

ELECTRIC CONTROL CIRCUIT

The invention relates to a myoelectric control circuit for at least one output control element, preferably an orthosis, with an amplifier stage controlled by the myosignals. The myoelectric control circuit of the type of interest here should also find application for the control elements of an adjustable work surface, a prosthesis or such like.

For the correct control of an output control element into two different operating conditions, for example, of the servomotor of an orthosis in the direction "open" and "close" of the hand, two myosignals, from two different groups of muscles, are generally sufficient.

Obtaining the desired number of mutually independent myosignals however entails considerable difficulties in the case of persons injured in the cervical spine, or in the case of higher or complete amputations, where, as a rule, all myosignals must be derived from a single group of muscles. The additional difficulty then arises that for injuries of this type it is generally difficult to activate a muscle whose motor functioning is partially faulty over a relatively lengthy time period as is required for the known control circuits.

One of these known control circuits works in such a fashion that the signals of a single muscle are utilized alternately for the control of the opening and closing process respectively.

Further, a control circuit is known in which the output control element can assume its other operating condition only when the previous operating condition is totally completed, that is, the output control element has been mechanically braked into the rest position. In case of an artificial hand this means, for example, that the reversal of the direction of movement from "closing" to "opening" can only take place when the motor has been braked to standstill condition when grasping an object.

These two control systems share the common disadvantage that the patient does not have the ability to choose a new operating condition independent of the last previous operating condition in each position of the output control element. Further, for example in the case of an orthosis, independently of how the myosignal itself is constituted, a closing process must always be followed by an opening process, then a closing process must again follow, etc. Furthermore, the first known control circuit has the disadvantage that the muscles from which the myosignal is derived must remain activated, that is, tensed, during the whole duration of the movement.

It is the object of the present invention to avoid these disadvantages.

The present invention relates to a control apparatus for activating at least one output control element in response to a myoelectric input signal. It comprises threshold circuit means responsive to the myoelectric input signal for furnishing a threshold output signal while the myoelectric input signal has an amplitude exceeding a predetermined amplitude. It further comprises timing means connected to the threshold, means for furnishing a timing signal for a predetermined time interval following receipt of the threshold output signal. Comparator means are provided which are connected to the threshold circuit means and the timing circuit means, for furnishing a first comparator output signal when the duration of the threshold output signal exceeds the predetermined time interval and a second comparator output signal when the duration of the threshold output signal is less than the predetermined time interval. Finally, connecting means are provided for connecting the output control element to the comparator means in such a manner that the operation thereof is dependent upon first and second comparator output signals.

The above-described apparatus has the advantage that the operating state of the output control element depends upon the characteristic of the myosignal, that is, upon its length. By appropriate activation and accordingly generation of a shorter or longer myosignal relative to the preselectable pulse duration, the same operating conditions of the output control element can be chosen sequentially, again and again, which, for example, in the case of an orthosis, is of particular importance for additional gripping following the end of a closing process.

Each of the myoelectric input signals has an amplitude corresponding to the tension in a predetermined muscle and a leading edge having a slope corresponding to the rate of change of the tension in the muscle. In a particularly advantageous further embodiment of the present invention, the above-mentioned comparator means constitutes first comparator means. Second comparator means are provided which are responsive to the myoelectric input signal for furnishing a third and fourth comparator output signal, respectively, when the slope of the myoelectric input signal is greater than and less than a predetermined slope. In this embodiment, the connecting means comprises means for connecting the output control element to the first and second comparator means in such a manner that the operation thereof is controlled by the first, second, third and fourth comparator output signals.

In this manner, a further parameter of the myosignals in addition to their duration can be used for the control of the output control elements. If the myosignal increases rapidly, that is, if a steep leading edge is present, the two threshold detector circuits will respond immediately one after the other. For a slowly rising myosignal, that is, for a leading edge having a relatively small slope, a correspondingly larger time interval will occur between the response times of the two threshold detector circuits. Since this time interval in accordance with the invention is now compared with a predetermined pulse duration and this occurs independently of the first comparison, it is possible thereby to control for example the intensity of the operating condition of the output control member, for example the closing speed of an orthosis.

In the following, the invention will be explained in a particular example with reference to the drawings.

Figure 6:
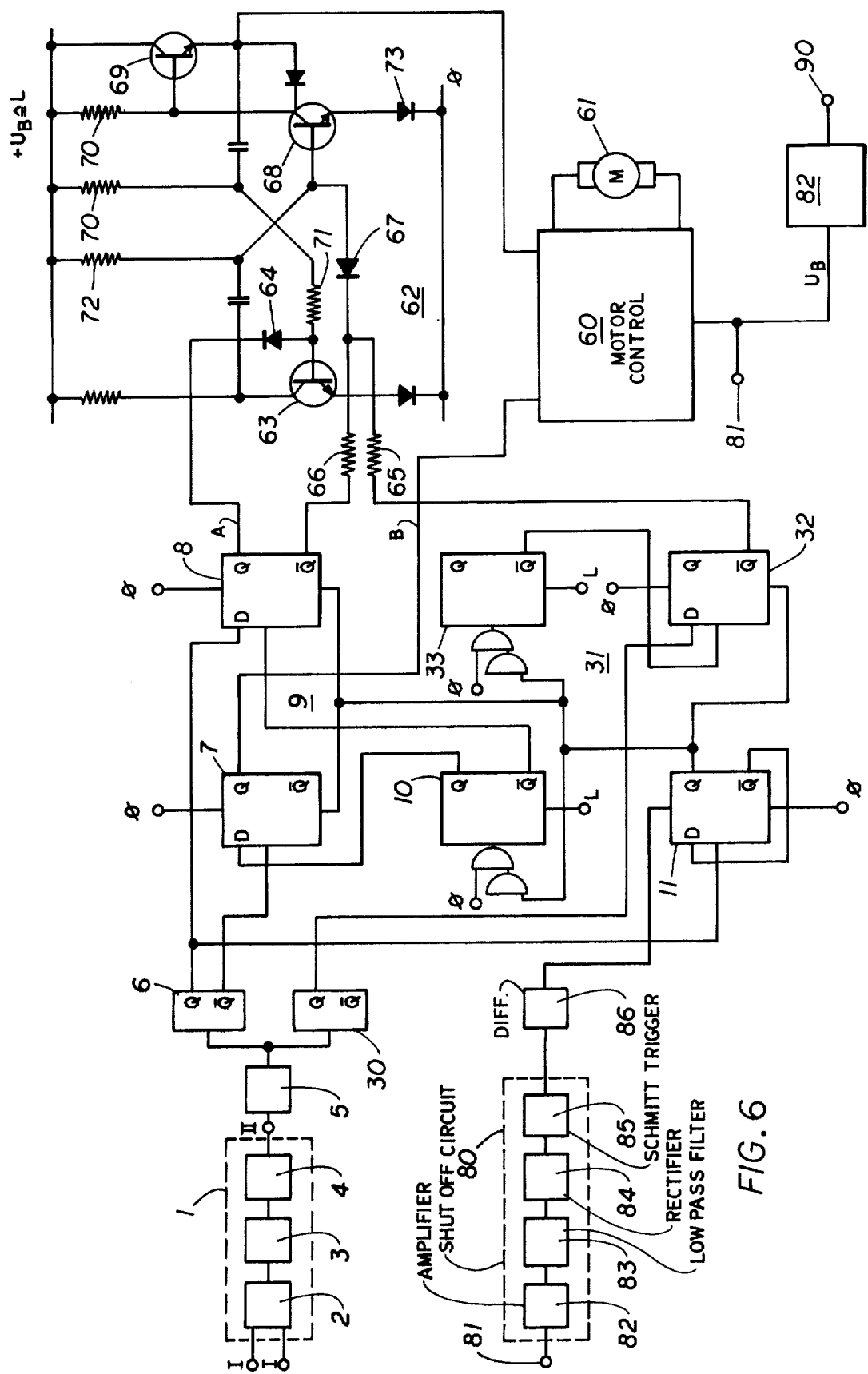

FIG. 1 shows a first embodiment of the control circuit in accordance with the present invention, partially in block form, FIGS. 2a to 2d show the voltage variations at several points in the circuit of FIG. 1 for different operating conditions of the output control element, FIG. 3 is a further embodiment in accordance with the present invention, FIGS. 4a to 4e show voltage variations at several points of the circuit in accordance with FIG. 3, again for different operating conditions of the output control element, FIG. 5 shows a circuit for a possible application for the control circuit according to FIG. 3, FIG. 6 a further embodiment of the control circuit in accordance with the present invention, which is particularly suitable for the motor control of an orthosis or prosthesis.

In FIG. 1, reference numeral 1 denotes an amplifier for a myosignal applied at terminal I, the myosignal being derived from a group of muscles in conventional fashion by means of electrodes. This amplifier comprises a preamplifier stage 2, a hum filter 3, and an output amplifier stage 4 with adjustable gain.

To the output of amplifier 1 is connected a rectifier stage 5, which in turn controls a threshold detector circuit 6. Suitably, the threshold detector stage 6 is a Schmitt trigger. The threshold detector circuit 6 has a non-inverting output denoted by Q and an inverting output denoted by $\overline{Q}$.

A bistable multivibrator circuit 7, 8 is connected to each output of threshold detector circuit 6. The non-inverting output Q of threshold detector circuit 6 is connected with the data input, D, of multivibrator circuit 8 and the inverting output $\overline{Q}$ of threshold detector circuit 6 is connected with the clock input of multivibrator circuit 7. When in the following a D input of a bistable multivibrator is discussed, an input is to be understood whose condition is transferred to the non-inverting output upon triggering of the clock input of the bistable multivibrator circuit with a positive going pulse edge. Further, the control circuit in accordance with FIG. 1 contains timing means, namely a monostable multivibrator circuit 10. Bistable multivibrators 7 and 8 form a comparator circuit 9. In addition, a bistable multivibrator circuit 11 is supplied. The input side of the monostable multivibrator circuit 10 is so connected that it responds only to negative going pulse edges. The clock input of bistable multivibrator circuit 11 is connected to the non-inverting output Q of threshold detector circuit 6. The data input, D, of multivibrator circuit 11 is connected to the inverting output $\overline{Q}$, so that the multivibrator circuit 11 works as a binary counter having a single stage, which will be discussed further below. The non-inverting output, Q, of multivibrator circuit 11 is connected both to the input of monostable multivibrator circuit 10 and to the clear inputs of multivibrator circuits 7 and 8.

The monostable multivibrator 10 has a non-inverting output denoted by Q which is connected to the data input, D, of multivibrator circuit 7, as well as an inverting output $\overline{Q}$, which is connected to the clock input of multivibrator circuit 8. The non-inverting outputs denoted by Q of multivibrator circuits 8 and 7 respectively denote the control outputs A and B, for, respectively, one or a plurality of output control elements. The set inputs of multivibrator circuits 7 and 8 as well as the set and clear inputs of multivibrator circuit 11 are connected to logic "0", and the clear input of 10 is connected to logic "1". The non-inverting output Q of bistable multivibrator circuit 11 is brought out as an output terminal C, which is in logic "0" condition when outputs A or B are activated, and, when the opposite is true, assumes the logic 1 condition, whereby a further control command can be derived.

The functioning of the circuit is as follows. The myosignal furnished by the electrodes and present at terminal I is amplified and filtered in amplifier 1 and is present at terminal II in the form shown in FIG. 2a. In FIG. 2a, several sequentially appearing myosignals are shown, first a strong myosignal of long duration and subsequent short myosignals. When the myosignal which has been rectified in rectifier stage 5 exceeds the threshold of threshold detector circuit 6, then this circuit switches from its quiescent state $Q_O$, $\overline{Q}$ into its triggered state $Q_L$, $\overline{Q}_O$, where L denotes the logic "1" state, "0" the logic "0" state. The positive pulse edge hereby generated at the Q output of the threshold detector circuit 6 triggers the clock input of bistable multivibrator circuit 11. Let it now be assumed that the data input, D, of circuit 11 is set to condition 0. This condition is transferred by the positive pulse edge at the clock input of multivibrator circuit 11 to its Q output so that this is switched from its reset $Q_L$ state into the $Q_O$ state. The hereby generated negative pulse edge triggers the monostable multivibrator circuit 10 for a predetermined time interval T1, preferably 500 msec. The Q output of monostable multivibrator circuit 10 therefore assumes the condition logic 1 during this predetermined time interval, while the inverting input $\overline{Q}$ of the same circuit assumes the 0 condition.

Crucial for determining whether output terminal A or B is activated by the applied myosignal is, whether the pulse generated by monostable multivibrator circuit 10 ends earlier or later than the myosignal applied to threshold detector circuit 6. The latter signal is herein called the myoelectric input signal.

If the pulse generated by monostable multivibrator circuit 10 ends before the threshold detector circuit 6 returns to its quiescent state, that is, prior to the ending of the myosignal, then upon ending of the pulse generated by monostable multivibrator circuit 10, the $\overline{Q}$ output of same returns to the logic 1 condition. This positive pulse edge triggers the clock input of bistable multivibrator circuit 8 and the logic 1 condition at its data input D - the myosignal is still present, the Schmitt trigger 6 is activated - is transferred to the Q output of 8, and output terminal A is energized. These relationships are illustrated by those pulses according to FIGS. 2b to 2d, which are associated with the first myosignal of FIG. 2a; the duration of the myosignal is denoted by $\tau$.

If on the contrary the myosignal ends before the pulse generated by monostable multivibrator circuit 10, then the threshold detector stage 6 flips back while the logic 1 condition still exists at the data input D of bistable multivibrator circuit 7. Because of the positive pulse edge created at the $\overline{Q}$ output of threshold detector stage 6, the logic 1 condition is transferred from the D input to the Q output of multivibrator circuit 7 and output terminal B is energized. These relationships are illustrated by the pulses in FIGS. 2b to 2d which are associated with the third myosignal of FIG. 2a.

Output A or B now remains energized until the next subsequent myosignal again triggers the threshold detector circuit 6. Since for the bistable multivibrator circuit 11 the Q output is connected with the data input D and this multivibrator circuit is thus connected as a single stage binary counter, the positive pulse edge then appearing at the Q output of threshold detector circuit 6 causes the logic 1 condition at the data input of bistable multivibrator 11 to be transferred to the Q output of same. The Q output is connected to the clear inputs of multivibrator circuits 7 and 8, so that these also now assume the logic 1 condition and are switched back to their reset condition. These relationships of the ending of the energization of outputs A or B are illustrated by the pulses of FIGS. 2b to 2d which are associated with the second and fourth myosignals respectively in FIG. 2A.

Thus, it is possible by means of the embodiment in accordance with the present invention shown in FIG. 1 to energize one or the other of outputs A or B in dependence upon whether the applied myosignal has a shorter or longer time duration than a predetermined pulse duration. Since the switching off of the control circuit results from the beginning of the myosignal, its time duration is negligible for this purpose.

Since, as has been explained above, the resetting of the bistable multivibrator circuits 7, 8, which operate as time comparators, to their original state results from triggering of multivibrator circuit 10 by the next following myosignal, it makes no difference what the shape of a myosignal following such a "reset" myosignal is, all possible conditions of the control circuit can again be chosen.

In the embodiment of the present invention shown in FIG. 3, those parts which correspond to the embodiment in accordance with FIG. 1 have the same reference numerals. As can be seen from FIG. 3, this circuit has the same circuit action as that according to FIG. 1, that is, outputs A and B of multivibrator circuits 7, 8 are energized in dependence upon whether the myosignal is shorter or longer than the duration T1 of the pulse generated by monostable multivibrator circuit 10. In addition, a further threshold detector circuit 30 is provided whose threshold is higher than that of threshold detector circuit 6. In a preferred embodiment, threshold detector circuit 30 constituting second threshold circuit means is also a Schmitt trigger. The input of threshold detector circuit 30 is connected with that of threshold detector circuit 6, so that both threshold detector circuits can be controlled by the input signal. The non-inverting output of circuit 30 is connected to a further comparator circuit 31, while the inverting $\overline{Q}$ output is left unconnected. The comparison circuit 31 comprises a bistable multivibrator circuit 32, with an inverting and a non-inverting output, and a monostable multivibrator circuit 33.

The data input, D, of bistable multivibrator circuit 32 is connected to the non-inverting output Q of threshold detector circuit 30. The clock input of circuit 32 is connected to the inverting output of monostable multivibrator circuit 33. The input of monostable multivibrator circuit 33 responds to negative going pulse edges and is connected to the non-inverting output, Q, of 11, which in turn is connected to the clear input of bistable multivibrator circuit 32 as well as to output terminal C. The outputs A and B of bistable multivibrator circuits 8 and 7 are logically connected with the inverting and non-inverting output of bistable multivibrator circuit 32 by AND gates 34 – 37 to four control element outputs D to G.

Functioning of the control circuit in accordance with the present invention as shown in FIG. 3 is the following. As was explained in relationship to FIG. 1, output A is energized when the duration $\tau$ of the myosignal is larger than the duration T1 of the pulse generated by monostable multivibrator circuit 10; the output B is energized, that is, is in the logic 1 state, when the duration $\tau$ of the myosignal is smaller than the pulse duration T1. However now, upon appearance of a myosignal, threshold detector circuit 6 triggers not only the monostable multivibrator 10 but also monostable multivibrator 33 connected to the input of monostable multivibrator 10. The monostable multivibrator 33 generates a pulse for a time duration T2 which preferably is 50 msec; the $\overline{Q}$ output of monostable multivibrator 33 is at zero for this pulse duration T2. The threshold detector 30, because of its higher threshold, will respond later than threshold detector circuit 6 and in particular for a steeply rising myosignal within a shorter, and for a low slope, slowly rising myosignal within a longer time interval. This time interval existing between the response of circuits 6 and 30 is hereinafter denoted $\Delta \tau$. In the reset condition of multivibrator 32, its Q output is at zero and its $\overline{Q}$ output at logic 1. After triggering of threshold detector circuit 30, the D input of multivibrator 32 is preset to logic 1. If threshold detector circuit 30 has thus responded within T2, that is if $\Delta \tau <$ T2, then, upon ending of the pulse generated by monostable multivibrator circuit 33 because of the positive pulse edge then appearing at the $\overline{Q}$ output of monostable multivibrator circuit 33, the logic condition at the Q and $\overline{Q}$ output of 32 changes. A logic 1 thus appears at one input of gate 36 as well as gate 37.

Which of the two gates now transfers logic 1 to its output depends upon whether the applied myosignal is a long or short signal relative to the pulse duration T1. If the signal duration $\tau$ exceeds that of T1, that is, if it is a long signal, then output terminal A is energized, AND gate 37 is conductive and the output terminal D is energized. If the signal duration $\tau$ is smaller than T1, then B is at logic 1, gate 36 becomes conductive and output F is energized. This circuit behavior is summarized below in the form of a truth table, wherein the leading edge of the input myosignal is called "steep", when the threshold detector circuit 30 responds within a time interval $\Delta \tau$ which is smaller than the duration T2 of the pulse generated by monostable multivibrator circuit 33.

| Pulse | Leading Edge | Gate | Gate Inputs | Energized Output |
|---|---|---|---|---|
| long | low slope | 34 | A; $L(\tau > T1)$<br>$\overline{Q}_{32}$; $L(\Delta \tau > T2)$ | D |
| short | low slope | 35 | B; $L(\tau < T1)$<br>$\overline{Q}_{32}$; $L(\Delta \tau > T2)$ | E |
| short | steep | 36 | B; $L(\tau < T1)$<br>$Q_{32}$; $L(\Delta \tau < T2)$ | F |
| long | steep | 37 | A; $L(\tau > T1)$<br>$Q_{32}$; $L(\Delta \tau < T2)$ | G |

In the following, the case is explained in which the threshold detector circuit 30 only responds when the pulse generated by monostable multivibrator circuit 33 already has ended. In this case, the D input of multivibrator 32 is still at zero when the $\overline{Q}$ output of monostable multivibrator 33 changes from zero to logic 1 at the end of the pulse, so that this condition is transferred to the Q output multivibrator of 32, and the inverting output $\overline{Q}$ of multivibrator 32 and thus one of the inputs of gates 35 and 34, remains in the condition of logic 1. In this case, the leading edge of the myosignal is said to have a low slope; if a long myosignal is concerned (output A energized), gate 34 is conductive, if a short myosignal is concerned (output B energized), gate 35 becomes conductive. These relationships can equally well be derived from the above truth table.

Advantageously, the rectifier stage 5 is an average value rectifier. This has the advantage relative to a peak rectifier, that the ripple of the DC voltage is substantially less for the same integration time constant. In order to reproduce the steep leading edges which are required for the control, a small integration time constant must be chosen in the present case, which for the case of a peak rectifier can lead to an excessively high ripple of the rectified voltage and thus to a multiple triggering of the threshold detector circuits 6, 30 and control errors resulting therefrom.

In FIG. 4a, the first myosignal is a "long" and "steep" signal; the third signal shown in FIG. 4a is a "long" and "low slope" myosignal. The second and fourth myosignals there illustrated are stop signals, similar to FIG. 2a. FIGS. 4b to 4e show the voltage variations associated with these myosignals and in particular FIG. 4b shows the voltage variation at the Q output of threshold detector 6, FIG. 4c the voltage variation at the Q output of threshold detector 30, FIG. 4d the voltage variation at $\bar{Q}$ output of monostable multivibrator circuit 33, FIG. 4e the voltage variation at output G or at output D.

Since, as in the circuit according to FIG. 1, the bistable multivibrator circuit 11 of the reset circuit is connected in FIG. 3 as a binary counter (connection of the $\bar{Q}$ output to the data input D), here too the resetting of an energized output is effected by a subsequently appearing myosignal, independently of its specific shape. Because of the connection of the Q output of bistable multivibrator circuit 11 to the clear input of multivibrator 32, upon application of a switching off myosignal to the bistable multivibrator circuit 11, the logic 1 condition to which the Q output of 11 is switched is applied not only to the clear inputs of multivibrators 7 and 8 but also to that of multivibrator 32, so that these multivibrators are switched back to the reset state and the previously activated output is reset to zero. The circuit is now again ready for energization by means of a control myosignal (first selected one of the myoelectric input signals).

A possible example for the application of the myoelectric control circuit according to the present invention as shown in FIG. 3 is shown in FIG. 5. There, the control circuit according to FIG. 3 is designated by 50, its outputs D and G being shown as external terminals. DC motors 55 and 56 are provided as output control elements which, controlled by relays 51 to 54 which are connected to outputs D to G, can be driven in one or the other direction of rotation. These DC motors 55 and 56 may be the driving motors of an adjustable work surface. It is also possible to use this arrangement for visual quality control, wherein the one motor 55 is used as a servomotor for the optic system and the second motor is utilized for marking or removing flawed work pieces.

FIG. 6 shows a further possible application of the circuit according to FIG. 3 and specifically for the control of an orthosis or prosthesis. The same building elements again are designated by the same reference numerals. In variation to the circuit according to FIG. 3, there is no logic interconnection of the outputs by means of AND gates. Instead, the Q output of bistable multivibrator circuit 7, that is the B output, is directly applied to a motor control 60 which is indicated in block form only. The servomotor for the orthosis or prosthesis is denoted by 61 and is driven in the "open" direction of, e.g., an orthosis when the Q output of multivibrator 7 (output B according to FIGS. 1 and 3) is energized, that is, is in a logic 1 condition.

Energization of the motor control 60 by multivibrators 8 and 32 takes place over a control circuit 62 which is constructed as a multivibrator circuit. The Q output of multivibrator 8, that is, the output A according to FIGS. 1 to 3, is connected through a diode 64 to the base of one of the multivibrator transistors 63 of the above-mentioned multivibrator circuit. The Q output of multivibrator 32 is connected with the $\bar{Q}$ output of multivibrator 8 through a series connection of two equally large resistors 65, 66. The common point of both resistors is connected via a diode 67 to the base of the other multivibrator transistor 68 of control circuit 62. Transistor 69 serves to increase the slope of the pulses generated by control circuit 62.

If output B is energized, then A (that is Q8) is at zero, diode 64 is poled in the conductive direction and current flows from $+V_B$ through resistors 70, 71 to the Q output of multivibrator 8, a diode connected into the emitter lead of transistor 63 preventing the base of 63 from drawing current; transistor 63 is thus blocked, the other transistor 68 of the multivibrator circuit accordingly assumes the complementary condition and is conductive, so that its collector and accordingly the associated input of the motor control is substantially at zero.

If however output A is energized, that is, if the multivibrator circuit 62 receives a logic 1 from the Q output of multivibrator 8, then the former applies a different signal to the motor control 60 depending upon the condition of the $\bar{Q}$ output of bistable multivibrator circuit 32, so that motor 61 is driven in the direction "close" for example of an orthosis, with two different speeds.

When the multivibrator circuit receives a logic 1 from the Q output of 8, the cathode of diode 64 is also at logic 1, diode 64 is blocked, and the transistor is not impeded in its function. The $\bar{Q}$ output of multivibrator 8 and thereby one end of the voltage divider formed by resistors 65 and 66 is at zero. If now the $\bar{Q}$ output of multivibrator 32 assumes the condition zero, which is the case when a myosignal with a steep leading edge is present, then the cathode of diode 67 is also at zero, this diode will conduct and current flows over resistor 72. However, the emitter diode 73 prevents transistor 68 from drawing base current and becoming conductive, so that its collector and thus the input of motor control 60 is substantially at logic 1, the motor runs at a first speed in the closing direction.

If, however, the $\bar{Q}$ output of multivibrator 32 assumes the logic 1 state, which is the case for a myosignal having a low slope of the leading edge, then the cathode of diode 67 is at a potential of L/2, which voltage value in the designed circuit arrangement is sufficiently high that diode 67 blocks. Thus, in the present case, both diodes 64 and 67 are blocked so that both multivibrator transistors 63, 68 are ready for operation, the multivibrator circuit oscillates. The square wave voltage appearing at the collector of transistor 68 is applied to motor control 60 and this is driven in the closing direction with a lower speed compared to the previous case where the full direct voltage was available.

Thus the following operating conditions of, for example, an orthosis can be obtained. If short myosignals with a duration $\tau$ which is smaller than the duration T1 of the pulses generated by monostable multivibrator circuit 10 appear, then an opening of the orthosis results; for myosignals with a duration longer than T1, a rapid closing or a strong gripping results for steeply rising myosignals, a slow closing or soft gripping for slowly rising myosignals.

Whether a long or short myosignal with steep or low slope leading edge is present depends insofar on the discretion of the patient as this depends upon the way in which the patient tenses the muscles connected to the electrodes. The advantage is also that the muscle in the present case does not have to be activated during the total operating time of the motor. Rather, the activation of the muscle for a time $\tau$   T1 suffices for putting the motor in operation, where T1 - as previously mentioned - is for practical purposes 500 msec. The control circuit remains in its circuit condition even after the ending of the myosignal. The motor continues to run in the chosen operating condition.

Shutting off of motor 61 takes place, in accordance with the control circuits of FIGS. 1 and 3, only by means of a sequentially appearing myosignal, which can be achieved by the patient by the tensing of the controlling group of muscles. Here too only the start of the myosignal is again definitive, the form or duration of the same being irrelevant.

By means of the bistable multivibrator circuit 32 which operates in the fashion of a binary counter, the whole control circuit is switched back to the quiescent condition, it subsequently being in condition to be set again by a myosignal of arbitrary duration or leading edge slope.

In addition to the above-explained motor shut-off, the control circuit according to FIG. 6 has an additional motor shut-off circuit 80. This is connected at 81 to the DC voltage supply which is formed by the input of a voltage stabilization circuit 82, whose output 90 constitutes the voltage supply for the multivibrator circuits. Since motor 61 of FIG. 6 is a commutator motor, during operation of the motor, the non-stabilized supply voltage VB has a ripple signal superimposed upon it.

The additional motor shut-off circuit 80 consists of an AC voltage amplifier 82, a low pass filter 83, a rectifier 84, and a Schmitt trigger 85. The Schmitt trigger has an inverting output, so that when a DC voltage level corresponding to the AC signal is applied at its input, the output of the Schmitt trigger is in condition zero. If the motor comes to a standstill, for example, when it is mechanically braked when reaching the closed position of the orthosis, then the AC signal too is absent, the Schmitt trigger 85 flips and its output assumes the logic 1 condition. Since however the output of the Schmitt trigger is connected to the set input of the bistable multivibrator circuit 11 through a differentiating element 86, the multivibrator circuit 11 is reset by this positive edge independent of the signals at its other inputs and with it the rest of the control circuit; the motor is shut off.

It is important in this connection that the low pass filter suppresses that ripple of the stabilized supply voltage which appears when the motor is driven with the pulse voltage. If the frequency of the pulse voltage, for example, is 25 kHz, then the filter suitably has a limiting frequency of approximately 2 kHz and a damping factor of approximately 80 dB.

If the shutting off of the motor took place by means of mechanical braking as a result of a gripping of the object in the above-described fashion, then the patient, with this control circuit in accordance with the present invention, has the possibility of additional gripping, which is of great importance for the true grasping of an object. The control circuit is preconditioned for energization by any arbitrarily formed myosignal by the logic 1 condition at the set input of 11. If now the patient activates the group of muscles strongly and for a time period exceeding T1, then the motor can be reactivated for a short time following the closed position of the orthosis and thus an additional gripping can be achieved; the shutting off then takes place again by means of 80.

The functioning of the control circuit according to FIG. 3 was explained relative to an orthosis; it is, however, not to be limited to this application. It, as well as the control circuits in accordance with the present invention shown at FIGS. 1 - 3, can also find use in the control of beds driven by electromotors, page turners for books, and the turning on and off as well as tuning of equipment as for example radio, television and dictation equipment.

What is claimed is:

1. Control apparatus for activating at least one output control element in response to a myoelectric input signal, comprising, in combination, threshold circuit means responsive to said myoelectric input signal for furnishing a threshold output signal while said myoelectric input signal has an amplitude exceeding a predetermined amplitude; timing means connected to said threshold means, for furnishing a timing signal for a predetermined time interval following receipt of said threshold output signal; comparator means connected to said threshold circuit means and said timing circuit means for furnishing a first comparator output signal when the duration of said threshold output signal exceeds said predetermined time interval and a second comparator output signal when the duration of said threshold output signal is less than said predetermined time interval; and connecting means for connecting said output control element to said comparator means in such a manner that the operation thereof is dependent upon said first and second comparator output signals.

2. Control apparatus as set forth in claim 1, wherein a sequence of myoelectric input signals is applied to said control apparatus, thereby creating a sequence of threshold output signals; further comprising reset circuit means connected to said threshold means and said comparator means, for resetting said comparator means, thereby terminating said first and second comparator output signals, in response to alternate ones of said threshold output signals.

3. Control apparatus as set forth in claim 2, wherein each of said threshold output signals has a leading edge and a trailing edge; and wherein said reset means is responsive to the leading edge of said alternate ones of said threshold output signals, whereby resetting of said comparator means is independent of the time duration of said alternate ones of said threshold output signals.

4. Control apparatus as set forth in claim 1, wherein each of said myoelectric input signals has an amplitude corresponding to the tension of a predetermined muscle and a leading edge having a slope corresponding to the rate of change of said tension in said muscle; wherein said comparator means comprises first comparator means; further comprising second comparator means responsive to said myoelectric input signal for furnishing a third and fourth comparator output signal, respectively, when said slope of said myoelectric input signal is greater than and less than a predetermined slope; and wherein said connecting means comprise means for connecting said output control element to said first and second comparator means in such a manner that the operation thereof is controlled by said first, second, third, and fourth comparator output signals.

5. Control apparatus as set forth in claim 4, wherein said threshold means comprises a first threshold circuit for furnishing a first threshold output signal when said myoelectric input signal has an amplitude exceeding a first predetermined amplitude; wherein said timing means comprises first timing means for furnishing a first timing signal for a first predetermined time interval following receipt of said first threshold output signal;

and wherein said second comparator means comprises second threshold circuit means for furnishing a second threshold output signal when the amplitude of said myoelectric input signal exceeds a second predetermined amplitude larger than said first predetermined amplitude, second timing means for furnishing a second timing signal starting with receipt of said first threshold output signal and ending with receipt of said second threshold output signal, third timing means for furnishing a third timing signal for a second predetermined time interval following receipt of said first threshold output signal, and means for furnishing said third and fourth output signals when the time duration of said second timing signal is less than and greater than, respectively, the time duration of said third timing signal.

6. Control apparatus as set forth in claim 5, wherein said first and second timing means each comprise a monostable multivibrator.

7. Control apparatus as set forth in claim 4, wherein said connecting means comprises a plurality of logic circuits.

8. Control apparatus as set forth in claim 7, wherein said output control element is the motor control of a servomotor; and wherein said logic circuits connect said motor control to said first and second comparator means in such a manner that the direction of rotation and speed of said servomotor are controllable by said first, second, third and fourth comparator output signals.

9. Control apparatus for controlling the operation of at least one output control element in response to a sequence of myoelectric input signals, comprising, in combination, first means responsive to said myoelectric input signals for furnishing output signals in response to first selected ones of said myoelectric input signals; second means responsive to said myoelectric input signals and connected to said first means, for terminating the furnishing of said output signals in response to second selected ones of said myoelectric input signals each following a corresponding one of said first selected ones of said myoelectric input signals in said sequency, whereby activation of said output control element is stopped in response to alternate ones of said myoelectric input signals.

10. Control apparatus as set forth in claim 9, wherein said first means comprises at least one bistable circuit having a set state for furnishing said output signal and a reset state; and wherein said second means comprises reset circuit means for switching said first means to said reset state in response to said second selected ones of said myoelectric input signals.

* * * * *